US 6,495,315 B2

(12) United States Patent
Hildreth et al.

(10) Patent No.: US 6,495,315 B2
(45) Date of Patent: Dec. 17, 2002

(54) CHANNEL FORMING TOXINS AS ANTIVIRAL AGENTS

(75) Inventors: James E. K. Hildreth, Woodstock, MD (US); Dzung H. Nguyen, Baltimore, MD (US); James Thomas Buckley, Victoria (CA)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 09/758,248

(22) Filed: Jan. 12, 2001

(65) Prior Publication Data

US 2002/0012671 A1 Jan. 31, 2002

Related U.S. Application Data

(63) Continuation of application No. 09/543,569, filed on Apr. 5, 2000, now abandoned
(60) Provisional application No. 60/128,541, filed on Apr. 9, 1999.

(51) Int. Cl.[7] .................................................. C12Q 1/70
(52) U.S. Cl. ...................... 435/5; 424/184.1; 424/187.1; 424/207.1; 424/208.1; 424/236.1; 424/239.1; 435/32
(58) Field of Search ........................... 424/184.1, 187.1, 424/192.1, 204.1, 207.1, 208.1, 236.1, 239.1, 832; 435/5, 71.3, 32; 530/300, 825

(56) References Cited

U.S. PATENT DOCUMENTS

| 5,777,078 A | | 7/1998 | Bayley et al. .............. 530/350 |
| 5,798,218 A | * | 8/1998 | Buckley ...................... 435/325 |
| 6,019,979 A | | 2/2000 | Bukrinsky et al. ........ 424/204.1 |

OTHER PUBLICATIONS

Ott D. Cellular proteins in HIV virions. Review Medical Virology (1997) vol. 3, pp. 167–180.*
Frank et al.t Acquisition of host cell–surface–derived molecules by HIV-1. AIDS (1996) vol. 10, No. 14, pp. 1611–1620.*
International Search Report, Intl. Appl. No. PCT/US00/09468, 2000, 7 pgs.
Saifuddin Mohammed et al., "Human Immundeficiency Virus Type 1Incorporates Both Glycosyl Phosphatidylinositol–anchored CD55 and CD59 and Complement–Mediated Destruction", *Jour. Of General Virology*, vol. 78, 1997, pp. 1907–1911.
Brodsky Robert A. et al., "Resistance of Paroxysmal Nocturnal Hemoglobinuria Cells To The Glycosylphosphatidylinositol–Binding Toxin Aerolysin", *Blood*, vol. 93, No. 5, 1999, pp. 1749–1756.
Nguyen Dzung, et al., "The Channel–Forming Toxin Aerolysin Neutralizes Human Immunodeficiency Virus Type 1", *Molecular Microbiology*, vol. 33, No. 3, 1999, pp. 659–666.
Ware et al., "Identification Of GPI–Deficient T Lymphocytes With PIG–A Mutations From Normal Persons Using In Viro Negative Selection With Aerolysin", *41st Annual Meeting of the American Soc. Of Hematology*, vol. 94, NO. 10, 1999, Abstract.
Mukhina et al., "Aerolysin Identifies Previously Undetectable PNH Populations In Patients With Aplastic Anemia", *Blood*, vol. 94, No. 10, 1999, Abstract.
Brodsky et al., "Improved Detection And Characterization Of Paroxysmal Nocturnal Hemoglobinuria Using Fluorescent Aerolysin", *Blood*, vol. 94, No. 10, 1999, Abstract.
Diep et al., "Glycosylphosphatidylinositol Anchors Of Membrane Glycoprotiens Are Binding Determinants For The Channel–Forming Toxin Aerolysin", *Jour. Of Biological Chemistry*, vol. 273, No. 4, 1998, pp. 2355–2360.
Chaudhary et al., "Selective Killing Of HIV–Infected Cells By Recombinant Human CD4–Pseudeomonas Exotoxin Hybrid Protein", *Nature*, vol. 335, No. 6188, 1988, pp. 369–372.

* cited by examiner

*Primary Examiner*—James Housel
*Assistant Examiner*—Ulrike Winkler
(74) *Attorney, Agent, or Firm*—Banner & Witcoff, Ltd.

(57) ABSTRACT

The infectivity of a population of enveloped viruses which comprise a glycosylphosphatidylinositol-anchored protein in their membrane can be reduced by employing certain toxins such as aerolysin, alpha toxin of *Clostridium septicum*, or enterolobin. Toxins which bind to glycosylphosphatidylinositol-anchored proteins inactivate such viruses. The toxins can be used to produce attenuated viral vaccines, to purge blood products, cells, or tissues of such viruses, and to detect viruses in samples.

11 Claims, 8 Drawing Sheets

FIG. 1B

| Aerolysin Virus | WT LD | WT tLD | WT JKT | T253C/A300C JKT | Y221G JKT |
|---|---|---|---|---|---|
| Oligomer → | | ▬ | | | — |

FIG. 2A

■ Jurkat HIV-1$_{RF}$
▨ LD⁻ HIV-1$_{RF}$
☐ tLD⁻ HIV-1$_{RF}$ y-axis: p24 (pg/ml)
x-axis: Aerolysin Concentration (nM) — Mock, 3.000, 0.300, 0.030, 0.003, 0.000

FIG. 2B y-axis: Syncytia (counts/hpf)
x-axis: Aerolysin Concentration (nM) — Mock, 3.000, 0.300, 0.030, 0.003, 0.000

CHANNEL FORMING TOXINS AS ANTIVIRAL AGENTS

RELATED APPLICATION

This application is a continuation of U.S. Ser. No. 09/543,569, now abandoned filed Apr. 5, 2000 and claims the benefit of Provisional Application Serial No. 60/128,541, filed Apr. 9, 1999, the disclosure of which is expressly incorporated herein.

The U.S. Government retains certain rights in this invention due to funding as provided by grants R01AI31806 and GM07626 awarded by the National Institutes of Health.

FIELD OF THE INVENTION

The invention is related to the area of antiviral agents. In particular it is related to the fields of channel-forming toxins and enveloped viruses.

BACKGROUND OF THE INVENTION

The channel forming toxin aerolysin has been shown to bind GPI-anchored proteins with high affinity ($K_d$ approx. $10^{-9}$ M for Thy-1; Cowell et al., 1997; Nelson et al., 1997, Diep et al., 1998). The glycosyl portion of the anchor is a binding determinant for the toxin (Diep et al., 1998). Aerolysin is secreted as an inactive 52 kDa precursor called proaerolysin by members of the bacterial genus Aeromonas (see Parker et al., 1996, for a recent review). Binding of aerolysin to GPI-anchored proteins promotes oligomerization of the toxin by concentrating it on the cell surface. As a result, cells displaying GPI-anchored proteins are far more sensitive to the toxin than those that do not (Nelson et al., 1998; Brodsky et al., 1999). The heptameric oligomers that are formed following binding are able to insert into the membrane, forming stable 1 nm channels that destroy the permeability barrier and cause cell death.

Human immunodeficiency virus (HIV) is the pathogenic agent that causes acquired immunodeficiency syndrome (AIDS). Efforts to cure HIV have yielded temporary and incomplete effects. There is a continuing need in the art for new therapeutic methods for treating human viruses, particularly those such as HIV which cause chronic infections.

SUMMARY OF THE INVENTION

It is an object of the invention to provide a method of treating a population of enveloped viruses which comprise a glycosylphosphatidylinositol-anchored protein in their membrane.

It is another object of the invention to provide an attenuated viral vaccine.

It is a further object of the invention to provide a method of purging a blood product, cell suspension, or tissue of enveloped viruses which comprise a glycosylphosphatidylinositol-anchored protein in their membrane.

It is yet another object of the invention to provide a method of detecting the presence of an enveloped virus in a sample.

These and other objects of the invention are provided by one or more of the embodiments below.

In one embodiment of the invention, a method is provided for treating a population of enveloped viruses which comprise a glycosylphosphatidylinositol-anchored protein in their membrane. The method comprises the step of contacting the population of enveloped viruses with a toxin which binds to glycosylphosphatidylinositol-anchors. The toxin is present in an amount sufficient to reduce infectivity of the population of viruses by at least 50%.

In another embodiment of the invention, an attenuated viral vaccine is provided. The vaccine comprises a population of enveloped virus particles which comprise a glycosylphosphatidylinositol-anchored protein in their membranes. The vaccine further comprises an oligomerized toxin bound to the glycosylphosphatidylinositol-anchored protein. The oligomerized toxin forms a channel. The infectivity of the population of enveloped virus particles is reduced by at least 50% compared to a population of the enveloped virus particles without the oligomerized toxin.

In another embodiment of the invention, a method is provided for purging a blood product, cell suspension, or tissue of enveloped viruses which comprise a glycosylphosphatidylinositol-anchored protein in their membrane. The method comprises the step of contacting the blood product, cell suspension, or tissue with a toxin which binds to glycosylphosphatidylinositol-anchors. The amount of the toxin is sufficient for the toxin to bind to at least 50% of the virus present in the blood product, cell suspension, or tissue.

In a further embodiment of the invention, a method is provided for detecting the presence of an enveloped virus in a sample. The method comprises the steps of contacting a cell-free extract of a sample with a a toxin which binds to glycosylphosphatidylinositol-anchors, allowing enveloped virus in the sample to bind to the toxin, and detecting the toxin which bound to the virus. The presence of toxin bound to virus indicates enveloped virus in the sample.

These and other objects of the invention provide the art with new methods and reagents for detecting, treating, and preventing the spread of enveloped viruses.

BRIEF DESCRIPTION OF THE DRAWINGS

FIG. 1B shows a Western blot performed on lysates of HIV-$1_{RF}$ derived from Jurkat, L D– or tLD– cells treated with wild type aerolysin, T253C/A300C mutant, or Y221G mutant. The bands correspond to aerolysin oligomers at 350 kDa and were detected by rabbit anti-aerolysin polyclonal antibodies. Viral inputs were all above 200 ng/ml of HIV-1 p24.

FIG. 4 shows that proaerolysin does not neutralize HIV-1. HIV-1 viral supernatant (>200 ng/ml) from Jurkat cells was treated with proaerolysin or aerolysin at the indicated dilutions and then added to target cells. p24 from the supernatant was measured two days post-infection using the method described in Example 3.

FIG. 5 indicates that aerolysin does not affect HIV-1 binding to soluble CD4Ig. HIV-1 from Jurkat cells at a concentration of 37 ng/ml p24, pre-treated with aerolysin dilutions, were incubated with CD4Ig or nonspecific human IgG. The CD4Ig and human IgG were then precipitated with SAC as described in Example 7. The bound virus was lysed and p24 was measured. This concentration of HIV-1 is on the order of 10-fold less than that neutralized by aerolysin at a concentration of 3 nM (cf. FIG. 3).

FIG. 6A indicates that $LD^-$ cells are resistant to aerolysin effects up to the maximum tested concentration of $3 \times 10^{-9}$ M aerolysin, while Jurkat and tLD− cells are highly susceptible to aerolysin induced cell death as measured by the MTS-assay. In FIG. 6B, $LD^-$ cells were incubated with aerolysin-treated virus (20 ng/ml p24) for 2 h before measuring cell viability.

DETAILED DESCRIPTION OF THE INVENTION

It is a discovery of the inventors that certain toxins bind with high affinity to viruses such as HIV-1 whose envelopes comprise GPI-anchored proteins. It is a further discovery of the inventors that toxins which oligomerize and form ion channels upon binding to such proteins are capable of neutralizing the infectivity of the viruses.

These discoveries make possible the treatment of certain viruses with a toxin to reduce the infectivity of the viruses. Viruses which can be employed in the invention are enveloped viruses containing GPI-anchored proteins in their membrane, such as HIV-1. Enveloped viruses are viruses which are released from eukaryotic cells by a process of budding, during which the viral particles become surrounded by a portion of membrane from the host cell that includes viral proteins. Examples of enveloped viruses include retroviruses such as HIV-1, Rous sarcoma virus, Semliki forest virus, vesicular stomatitis virus, herpes virus, influenza virus, flavivirus, and bunyavirus. Enveloped viruses for use with the invention have GPI-anchored protein in their membrane. Preferably the envelopes are unilamellar. GPI-anchored proteins are common in eukaryotic cells and can be obtained by a virus from the host cell membrane during budding. Examples of viruses whose envelopes contain GPI-anchored proteins are HIV-1, simian immunodeficiency virus (SIV), human cytomegalovirus (HCMV), and human T cell leukemia/lymphoma oncovirus type I (HTLV-1).

A population of viruses containing GPI-linked proteins in their membranes can be contacted with a toxin which binds to the GPI-linked proteins. A "population" of such viruses refers to a plurality of the viruses existing in any form consistent with treatment by a toxin to reduce their infectivity. For example, a population of viruses can be a suspension of virus particles present in a cell culture medium or other solution. A population of viruses can also be a pellet or a freeze-dried preparation containing the viruses. The population of viruses can be either in pure or impure form. If desired the viruses can be purified by any appropriate method known in the art either prior to or subsequent to treatment of the population of viruses with the toxin.

The population of viruses can be treated by certain toxins to reduce the infectivity of the population of viruses. The population of viruses is treated by exposure to the toxin in any manner which renders the infectivity of the population of viruses less than it would have been without the treatment. For example, the treatment can consist of contacting the population of viruses with the toxin by adding the toxin to a suspension containing the population of viruses in a culture medium under conditions which promote the binding of the toxin to the viruses. Once the toxin has bound to the viruses, their infectivity will be reduced by the bound toxin. Alternatively, the toxin can be added to cells from which the population of viruses are subsequently released, such that upon release, the viruses contain the bound toxin.

A variety of toxins are suitable for use in the invention A suitable toxin has the property of binding with high affinity to GPI-anchored protein in the membrane of the virus or host cell containing the virus and thereby inactivating the virus or rendering the infectivity of a population of such viruses less than it would have been without the bound toxin. While the invention is not limited to any particular mechanism, the loss of infectivity may be related to the formation of ion channels by the toxin, for example by oligomerization of the toxin to yield one or more pore-forming structures in the viral envelope. Alternatively, the loss of infectivity may be due to steric inhibition of virus binding to cellular receptors. Suitable toxins include any of the aerolysins of Aeromonas species (Parker et al., 1996), alpha toxin of *Clostridium septicum* Ballard et al., 1995), enterolobin of *Enterolobium contortisiliquum* (Fontes et al., 1997; Sousa et al., 1994; Sousa & Morhy, 1989), and variants of them which have the property of binding with high affinity to GPI-anchored protein in the membrane of the virus or host cell containing the virus and thereby inactivating the virus. Proaerolysin and some aerolysin variants bind GPI-anchored proteins but do not form channels. They can be used to bind, but they do not reduce infectivity of the virus.

A toxin binds to GPI-anchored proteins if, when contacted with cells or enveloped viruses, the toxin molecules associate with or non-covalently bond to GPI-anchored protein molecules or regions of the cell or viral membranes containing GPI-anchored proteins. A toxin binds selectively to GPI-anchored proteins if it binds to such proteins with higher affinity than to other proteins or binds to membrane regions containing GPI-anchored proteins with higher affinity than to other membrane regions. Typically a toxin will bind at least 2-fold, 3-fold, 5-fold, 10-fold, 100-fold, or 1000-fold more avidly to a GPI-anchored protein than to other proteins.

The infectivity of a population of viruses can be measured by determining the percentage of cells which become infected when exposed to a given dose of virus from the population of viruses. The multiplicity of infection for such measurements will preferably be less than 1 and more preferably less than $10^{-1}$ or $10^{-2}$. Infectivity can be expressed as the fraction or percentage of host cells which become infected. Alternatively, infectivity can be expressed as the amount of virus or viral protein produced by a given number of host cells, or as the number, fraction, or percentage of cells that die upon exposure to the virus. The infectivity of the population of viruses can be reduced according to the method of the invention by any amount. Preferably, a treatment will reduce the infectivity of a population of viruses by at least 50%, at least 70%, at least 75%, at least 80%, at least 85%, at least 90%, at least 95%, at least 97%, or at least 99%.

An attenuated viral vaccine according to the invention is a vaccine which comprises attenuated virus and which induces an immune response when administered to a human patient or an animal. The virus contained in the vaccine can be attenuated according to the invention by treatment with a toxin which binds to GPI-anchored proteins in the viral membrane. This can be accomplished by any of the methods described above. The virus is attenuated when the infectivity of a population of the virus is reduced by at least 30%, at least 50%, at least 70%, at least 75%, at least 80%, at least 85%, at least 90%, at least 95%, at least 97%, or at least 99%. The vaccine can be administered therapeutically to an infected individual or prophylactically to uninfected individuals. The vaccine can be administered by any suitable route, for example by oral or intranasal administrtion, or by intramuscular, intravenous, or transdermal injection. The vaccine can be lyophylized to enhance its stability. The vaccine can comprise an adjuvant, a potentiator, a stabilizer, a buffer or other substances suitable for safe and effective administration. The vaccine can also be combined with other vaccines into a combination vaccine.

A biological sample can be purged of enveloped viruses that comprise a GPI-anchored protein in their membrane. A biological sample can be a blood product, a cell suspension or other arrangement of cells obtained from any organism, or a tissue obtained from any organism. A blood product is whole blood or any cell, protein, or liquid fraction obtained from the whole blood or serum of a human or an animal, or any product derived from it. The sample can contain the virus to be purged, located in the extracellular portion of the sample. The biological sample can be subjected to the purging process whether or not the sample is known to contain enveloped viruses that comprise a GPI-anchored protein in their membrane.

Purging a sample that contains or possibly contains such viruses can be accomplished by contacting the sample with a toxin which binds GPI-anchored proteins so as to either functionally or physically remove the viruses from the biological sample. The sample is functionally purged if the infectivity of the viruses in the sample is reduced by at least 50%, at least 70%, at least 75%, at least 80%, at least 85%, at least 90%, at least 95%, at least 97%, or at least 99%. The sample is physically purged if the toxin binds to at least 50%, at least 70%, at least 75%, at least 80%, at least 85%, at least 90%, at least 95%, at least 97%, or at least 99% of the viruses in the sample, and at least 50%, at least 70%, at least 75%, at least 80%, at least 85%, at least 90%, at least 95%, at least 97%, or at least 99% of the bound viruses are then separated or removed from the sample. A variety of methods can be used to separate the viruses from the sample. These include binding the viruses to immobilized toxin which is bound to a solid support, such as the matrix of a chromatographic material, magnetic particles, the surfaces of a plastic container, polymer fibers, and the like. Alternatively, the toxin can be non-immobilized, e.g., added free in solution to bind to the viruses, and the toxin can then be separated using an immobilized receptor for the toxin, such as an antibody to the toxin. Alternatively, no separation step need be performed if the viruses contained in the sample are rendered non-infective upon binding to the toxin. The virus is rendered non-infective upon binding to the toxin if, at least 50%, at least 70%, at least 75%, at least 80%, at least 85%, at least 90%, at least 95%, at least 97%, or at least 99% of the viruses are bound to the toxin, and the infectivity is reduced by at least 50%, at least 70%, at least 75%, at least 80%, at least 85%, at least 90%, at least 95%, at least 97%, or at least 99%.

The presence of an enveloped virus in a sample can be detected by means of the selective binding of a toxin to GPI-anchored proteins in the viral envelope. The toxin can optionally be labeled, for example by incorporation of a suitable radiolabel into the toxin molecule or by covalently or non-covalently attaching to the toxin molecule a suitable fluorescent label. The binding of the toxin to the enveloped virus can be detected and used as an indication of the presence of the enveloped virus in the sample. Any biological sample suspected of harboring an enveloped virus can be used. For example, the sample can be blood, plasma, tissue, urine or other bodily fluid from a patient or an animal. The sample can also be a cell from a cell culture or cell suspension, or it can be an organ intended for transplantation. The entire sample or a portion of the sample can be processed to prepare a cell-free extract. The cell-free extract should be substantially free of whole cells and cell fragments which contain GPI-anchored proteins but should preferably contain a measurable fraction of enveloped virus present in the original sample. A measurable fraction of an enveloped virus is an amount which can be detected or quantified by the chosen method of detecting the virus, examples of which are described below. Any method known in the art can be used to produce a cell-free extract, such as homogenization of the sample followed by centrifugation, ultrafiltration, trapping the viral particles or non-viral contaminants on a column or other solid support, or any combination of such methods.

In order to detect the virus in the cell-free extract, the extract is contacted with toxin under conditions which favor the binding of the toxin to GPI-anchored proteins in the viral envelope. For quantitative determination of the amount of virus in a sample, the toxin is preferably labeled and in molar excess over the number of toxin binding sites in the sample, so that the amount of labeled toxin that binds provides an accurate representation of the number of enveloped viruses in the sample. For example, the toxin can be in at least 1.2-fold, 1.5-fold, 2-fold, 3-fold, 5-fold, 10-fold, 30-fold, or 100-fold excess over the number of viral toxin binding sites. The appropriate level of excess labeled toxin can be determined by adding increasing amounts of toxin to an extract containing a constant amount of enveloped virus. The level of toxin is sufficient if further increases in toxin do not alter the amount of virus detected.

In some embodiments, detection or quantification of the amount of virus-bound toxin employs separation of virus-bound toxin from unbound toxin, or from toxin bound to non-viral structures. Any separation technique known in the art can be used, such as centrifugation, ultrafiltration, trapping the viral particles or non-viral contaminants on a column or other solid matrix, or any combination of such methods. Following separation of virus-bound toxin, the toxin is detected. If the toxin is radiolabeled, for example using $^3$H, $^{14}$C, $^{32}$P, $^{35}$S, $^{125}$I or some other suitable radioisotope, then a method of detection is chosen which is suitable to detect the emitted radiation (e.g., scintillation counting or gamma counting). If the toxin is fluorescently labeled, then a suitable spectrofluorometric method can be used. In one embodiment, the binding of fluorescently labeled toxin to the enveloped virus is determined by quenching of fluorescence as the labeled toxin molecules oligomerize within the viral membrane. Immunological and enzyme-based methods can also be used to detect toxin bound to virus.

The method of detection can either be used non-quantitatively, to detect the presence or absence of the virus in the cell-free extract, or quantitatively, to detect the amount of virus in the cell-free extract. In either case, the sample under investigation should be compared to a control sample which is known to be free of enveloped viruses that bind the toxin. The amount of bound toxin in the control sample can be subtracted from the amount of label in the sample under investigation. The remaining toxin is representative of the presence and amount of enveloped virus in the cell-free extract. Based on the number of toxin molecules bound, and the number of toxin binding sites per virus, the number of virus particles in the extract and in the original sample can be readily determined.

Because the method of detecting enveloped viruses described above will give a cummulative measure of enveloped viruses containing GPI-anchored proteins, in some embodiments it will be desirable to subsequently perform other analyses to determine the type of viruses present. This can be accomplished by performing standard analyses such as immunological or electron microscopic analyses.

The above disclosure generally describes the present invention. A more complete understanding can be obtained by reference to the following specific examples, which are provided herein for purposes of illustration only and are not intended to limit the scope of the invention.

EXAMPLE 1

Binding of Aerolysin to HIV-1

This example demonstrates that aerolysin and proaerolysin toxins bind to HIV-1 virus using HIV-1 capture assays in which aerolysin or proaerolysin was substituted for the monoclonal antibodies (Gomez and Hildreth, 1993). HIV-$1_{RF}$ strain (obtained from Dr. Robert Gallo through the NIH AIDS Research and Reference Reagent Program) was used to chronically infect Jurkat, LD$^-$ and tLD$^-$ cells. Jurkat cells were purchased from the American Type Culture Collection (Rockville, Md.). CD4+ LD$^-$ cells (an EBV transformed B-cell line from a paroxysmal nocturnal hemoglobinuria (PNH) patient) and tLD$^-$ cells (LD$^-$ cells transfected with the *PIG-A* gene) were obtained from Dr. Robert Brodsky, Johns Hopkins University. All cell lines were maintained in RPMI 1640 medium (Gibco BRL, Life Technologies, Gaithersburg, Md.) supplemented with 10% fetal calf serum (FCS) (Hyclone, Logan, Utah), 2 mM L-glutamine, and 10 mM HEPES (cRPMI). Virus containing supernatants were collected from cultures at a cell density of 1–2×10$^6$/ml and passed through 0.45 micron filters. Virus production was measured by p24 ELISA after detergent lysis of supernatants. Control mouse myeloma IgG1 was purchased from Jackson Immunoresearch (West Grove, Pa.). Soluble recombinant CD4-immunoglobulin Fc chimera (CD4Ig) was obtained from Dr. Tim Gregory (Genentech, South San Francisco).

Native proaerolysin and the proaerolysin variants, Y221G, and T253C/A300C were purified according to a published procedure (Buckley, 1990). The T253C/A300C variant can bind normally, but it is unable to oligomerize and is therefore inactive (Rossjohn et al., 1998). The Y221G variant can bind and oligomerize like wild type, but it is unable to insert and form channels.

A previously described plate-based virus immunocapture assay was used with modifications (Nguyen and Hildreth, 1998). ELISA plates (Costar) were coated with 100 µl of control IgG1, native proaerolysin, T253C/A300C variant, or Y221G variant at 5.0 µg/ml in 50 mM Tris, pH 9.5. Plates were incubated at room temperature 12–15 h before removing supernatants and blocking wells with 200 µl of 3% BSA in PBS for 2 h at 37° C. After the wells were washed 6 times with PBS, 0.5% Tween-20, doubling dilutions of viral supernatants from Jurkat cells were added (100 µl/well) and incubated for 2 h at 37° C. Samples were removed and wells were washed six times with 150 µl of RPMI 1640. Captured viruses were lysed for 1 h at 37° C. with 100 µl of 1% Triton X-100, RPMI, 10% FCS. Viral lysates were stored at 4° C. until standard quantitative p24 ELISA was performed.

Figure 1A:
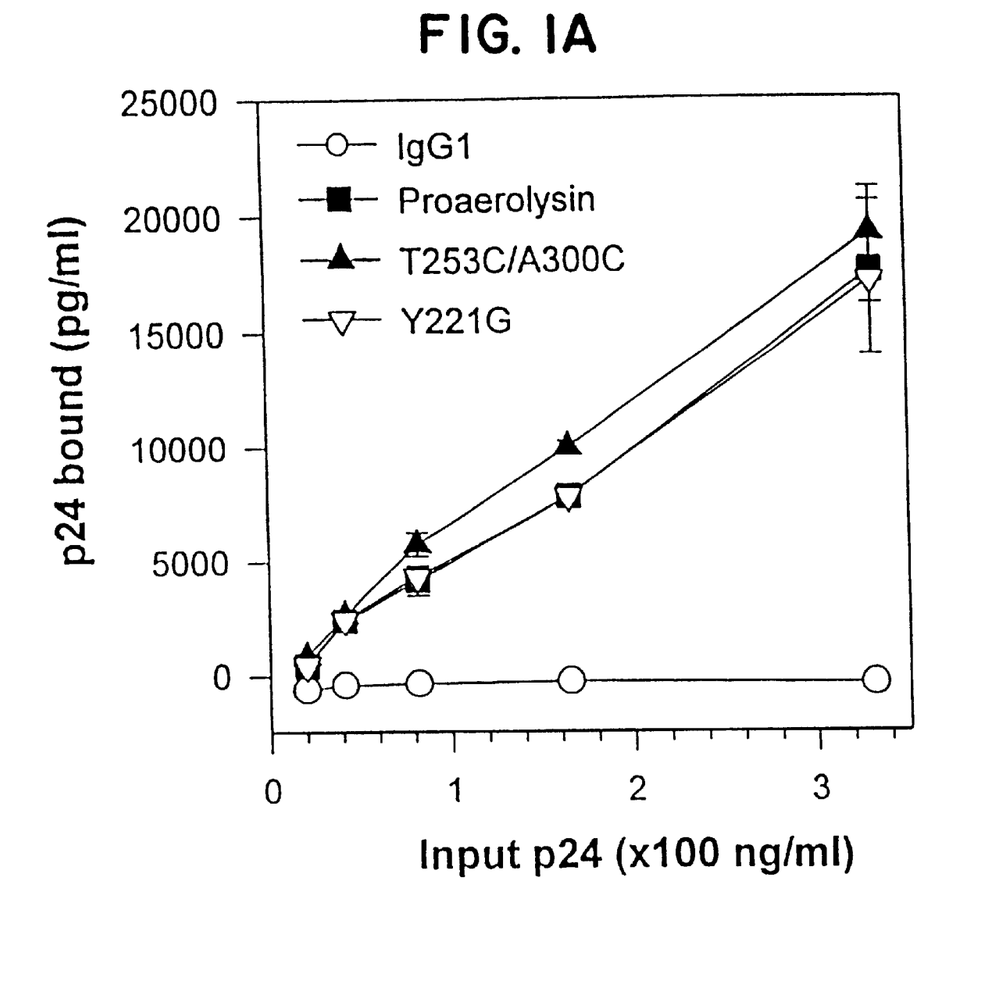
FIGS. 1A and 1B demonstrate the binding and oligomerization of aerolysin and proaerolysin to HIV-1 bearing GPI-linked proteins. In the experiment depicted in FIG. 1A, the binding of HIV-1 from Jurkat cells to proaerolysin and aerolysin mutants was determined as described in Example 1. The graph shows the amount of p24 bound versus the total input of p24. Mouse IgG1 was used as a nonspecific control.

FIG. 1A shows that HIV-1 produced by Jurkat cells bound specifically to proaerolysin-coated ELISA plates. There was no binding to mouse myeloma IgG used as a negative control.

EXAMPLE 2

Viral GPI-anchored Proteins are Required for Aerolysin Binding and Oligomerization When aerolysin binds to GPI-anchored proteins on target cells it oligomerizes to form 350 kDa heptamers. Since the oligomers are not disrupted by SDS-PAGE, their formation is easily monitored by immunoblotting with an anti-aerolysin antibody after electrophoresis (Howard and Buckley, 1982).

In 12×75 mm polypropylene tubes, 150 µl of virus-containing supernatants were added to 150 µl of aerolysin or aerolysin mutants Y221G and T253C/A300C (final concentrations 1×10$^{-9}$ M) in RPMI, 10% FCS and incubated at 37° C. for 1 h. PBS was added (500 µl), and tubes were then centrifuged in a Biofuge 15 (VWR, Baxter Scientific Products, West Chester, Pa.) for 1 h at 20,000 ×g. The wash was carefully removed and 500 µl of lysis buffer (50 mM Tris, 5 mM EDTA, 100 mM NaCl, 1% Triton X-100, pH 8) was added followed by incubation for 1 h at room temperature. SDS-PAGE was carried out as described by Neville (1971), and proteins were transferred onto nitrocellulose membranes for detection with ECL (Amersham Life Sciences, Inc., Arlington Heights, Ill.).

Figure 1B:
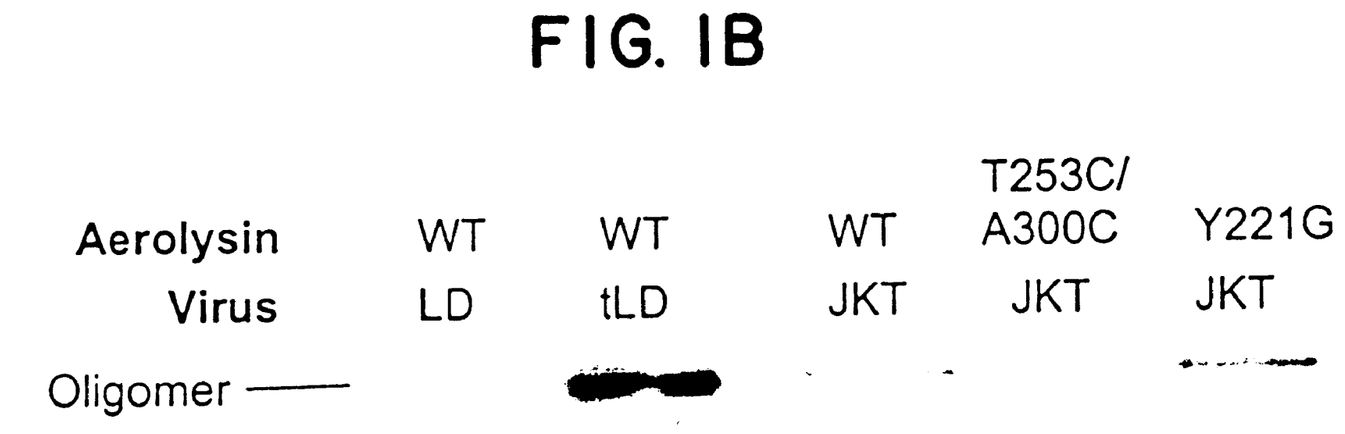

The results in FIG. 1B show that aerolysin oligomers were detected by immunoblotting after HIV-1 from Jurkat cells or tLD– cells was incubated with the toxin. This is evidence that aerolysin had bound to the virus and oligomerized.

Evidence that GPI-anchored proteins in the viral envelope were required for toxin binding and oligomerization was obtained using virus originating from PNH-derived LD$^-$ cells, which lack GPI-anchored proteins due to a mutation in the *PIG-A* gene that encodes an enzyme required for anchor synthesis. The results in FIG. 1B show that no oligomer was detected after incubating aerolysin with HIV-1 obtained from LD$^-$ cells. However the results in FIG. 1B also show that oligomer could be detected when virus was used that originated from the same cell line transfected with the PIG-A gene (tLD$^-$), which restores production of GPI-anchored proteins. Thus, aerolysin binds to and oligomerizes on HIV-1 particles that contain in their envelopes GPI-anchored proteins acquired during budding from cells with a functional PIG-A gene. HIV-1 produced from cells which lack GPI-anchored proteins do not bind aerolysin and no oligomers are formed.

EXAMPLE 3

Aerolysin Neutralizes HIV-1 in a GPI-anchored Protein-dependent Manner

Neutralization of infectivity by aerolysin and its variants was assayed by determining the amount of virus released after infecting LD$^-$ cells. The amount of p24 released into the culture medium was used to quantify production of HIV-1. In 12×75 mm polypropylene tubes, 250 µl of virus-containing supernatants (300 ng/ml p24) were added to 250

μl of aerolysin or proaerolysin dilutions (final concentrations: from $3\times10^{-9}$ to $3\times10^{-12}$ M) in RPMI, 10% FCS and incubated at 37° C. for 1 h. Tubes containing no virus or no aerolysin were used as controls. Fifty μl of target LD– cells ($4\times10^6$/ml in RPMI, 10% FCS) were added, followed by incubation for 12–15 h at 37° C., 5% $CO_2$. Cells were then washed twice with RPMI, resuspended in 1.0 ml RPMI, 10% FCS, and transferred to wells of a 24-well plate which was then incubated at 37° C., 5% $CO_2$ for 3 days. Following incubation, cells were pelleted by centrifugation. Five hundred μl of supernatant was removed and transferred to tubes containing 500 μl of 2% Triton X-100, RPMI, 10% FCS. p24 was measured using a standard p24 ELISA assay.

Figure 2A:
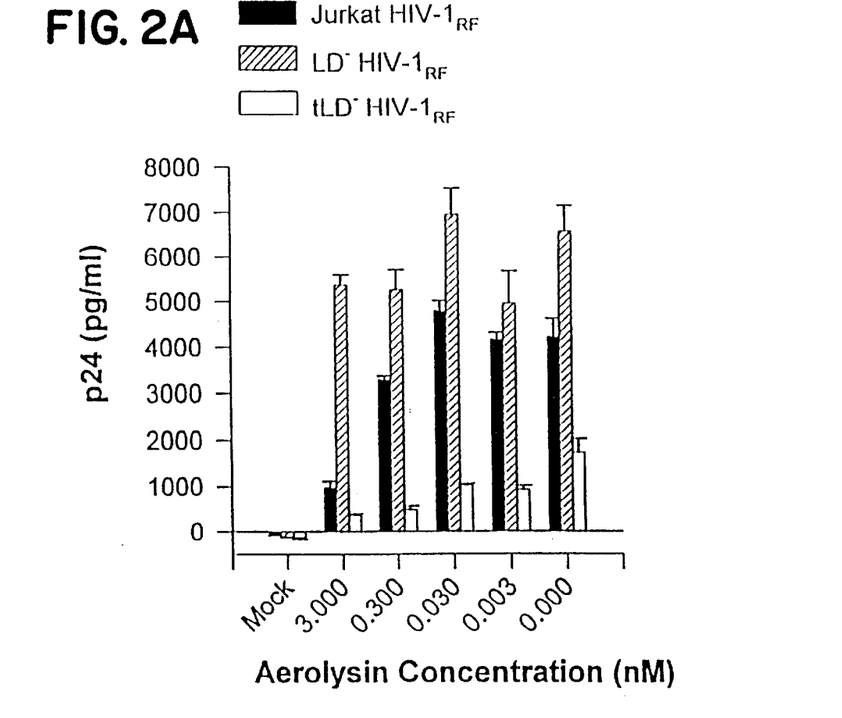
FIGS. 2A and 2B demonstrate that aerolysin neutralizes HIV-1 from GPI-anchor-positive Jurkat and tLD– cells, but not GPI-anchor-deficient LD– cells HIV-$1_{RF}$ was produced in Jurkat, LD–, and tLD– cells and used in neutralization assays as described in Example 3. The virus samples were treated with dilutions of aerolysin before being added to target cells (uninfected LD– cells). After washing, cells were incubated for 3 days before the production of p24 was measured (FIG. 2A) and syncytia were scored (FIG. 2B) in separate assays.

When HIV-1$_{RF}$ from either Jurkat cells or tLD$^-$ cells, both of which display GPI-anchored proteins, was exposed to concentrations of aerolysin ranging from 3 pM to 3 nM, the virus was neutralized in a dose dependent manner. The results in FIG. 2A show that significant neutralization occurred at toxin concentrations greater than 30 pM, corresponding to concentrations that have been shown to cause T cell death. In contrast, the same strain of HIV-1 originating from LD cells, which lack GPI-anchored proteins, was not susceptible to aerolysin neutralization, even at 100-fold higher concentrations (FIG. 2A). These studies were carried out using CD4+, CXCR4+LD$^-$ cells as targets for the virus, since those cells are resistant to the toxic effects of aerolysin (see FIG. 6A). Thus the neutralization we observed must have been due to an interaction of the toxin with the virus, rather than with the cell.

Figure 2B:
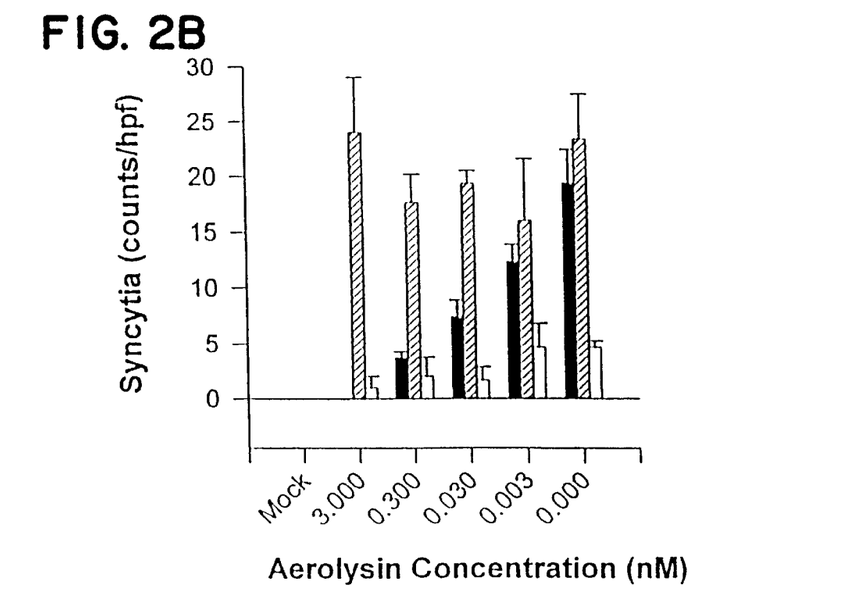

The effect of aerolysin on HIV-1 was confirmed in separate assays shown in FIG. 2B, in which syncytium formation in LD$^-$ cells was used as the measure of infectivity. The MTS cell viability assay quantifies the loss of viable cells resulting from viral infection. In a 96-well plate, 50 μl of virus supernatant (20 ng/ml of p24) was mixed with 50 μl of aerolysin dilutions ($10^{-8}$ to $10^{-11}$ M) and incubated for 1.5 h at 37° C. To each well, 50 μl of LD$^-$ cells ($1\times10^6$/ml) were added and allowed to incubate for 2 h at 37° C. One percent Triton X-100 was used as a positive control for cell death. The tetrazolium substrate was prepared as follows: 950 μl of 2 mg/m 3-(4,5-dimethylthiazol-2-yl)-5-(3-carboxymethoxyphenyl)-2-(4-sulfophenyl)-2H-tetrazolium (MTS) stock solution (Promega, Madison, Wis.), 50 μl of 0.92 mg/ml phenazine methosulfate (PMS) (Promega, Madison, Wis), and 4 ml of cRPMI. To each well 50 μl MTS-PMS solution were added and cells were allowed to incubate for 1 h at 37° C. Twenty μl of 10% Triton X-100 were then added to each well and allowed to incubate at room temperature for 30 min. Optical density was measured at 450 nm on a spectrophotometric plate reader (Cambridge Technology). Cell death is proportional to the optical density at 450 nm. Therefore, a reduction of infectivity corresponds to a proportional reduction in optical density at 450 nm.

The MTS cell viability assay showed that aerolysin inhibited infection by virus from Jurkat and tLD$^-$ cells but had no effect on virus from GPI-anchor-negative LD$^-$ cells. These results demonstrate that very low concentrations of the channel-forming protein can neutralize HIV-1 and that GPI-anchored proteins in the viral membrane confer susceptibility to neutralization by the toxin at these concentrations.

EXAMPLE 4
PI-PLC Treatment Reduces Virus Susceptibility to Aerolysin Neutralization Treating T cells with PI-PLC removes most of their GPI-anchored proteins and reduces their sensitivity to aerolysin (Nelson et al., 1997). To confirm that the neutralization of HIV-1 by aerolysin we observed in FIG. 2 was mediated by its binding to GPI-anchored proteins, we treated the virus with PI-PLC and repeated the above neutralization assays. Phosphatidylinositol-specific phospholipase C (PI-PLC) (Boehringer Mannheim, Indianapolis, Ind.), was added to viral supernatants (20 ng/ml p24) to a final concentration of 20–50 mU/ml followed by incubation for 16 h at 37° C. Treated and control samples were then used in aerolysin neutralization assays as described above.

Figure 3:
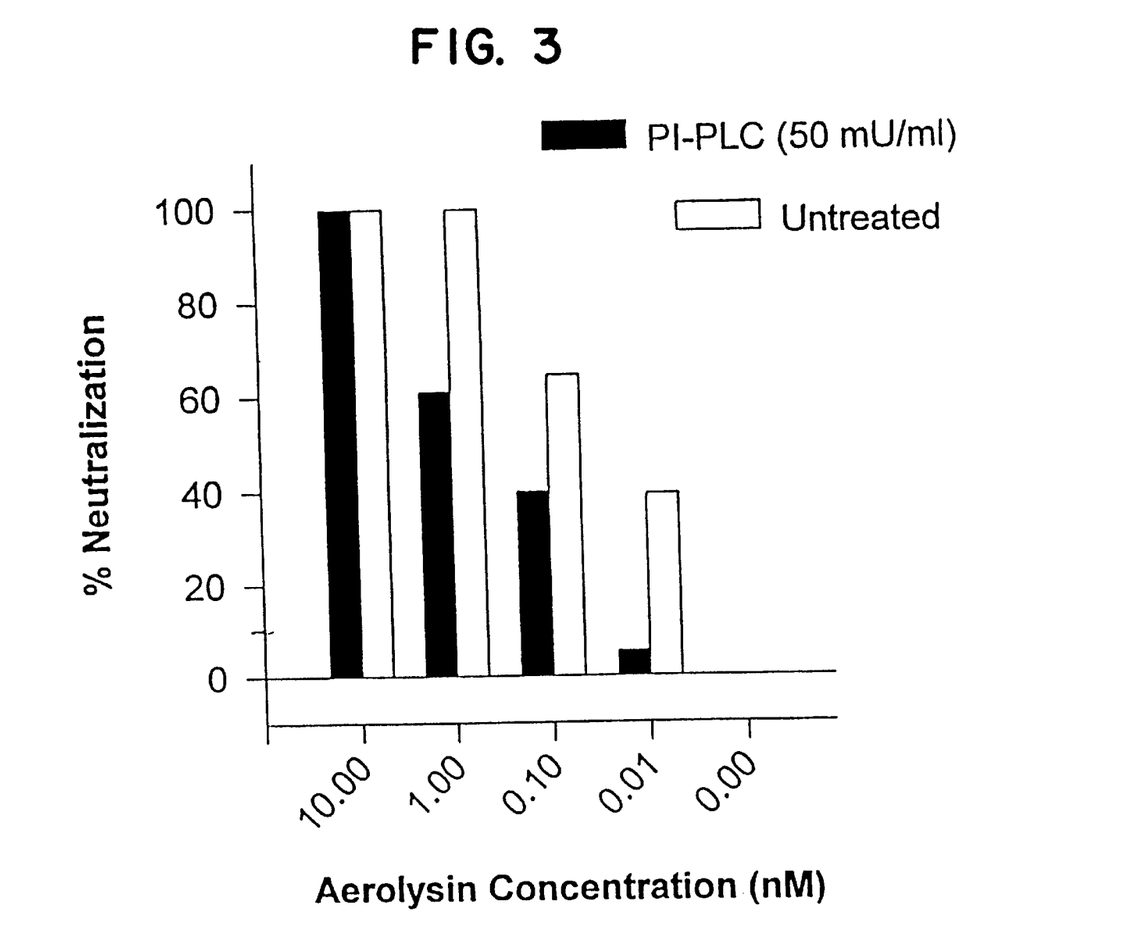
FIG. 3 shows that phosphatidylinositol-specific phospholipase C treatment reduces HIV-1 susceptibility to aerolysin neutralization. HIV-1 from Jurkat cells (20 ng/ml of p24) was treated with PI-PLC for 16 h before the addition of aerolysin dilutions. The virus neutralization assay was performed according to Example 3. The graph displays the percent neutralization of HIV-1 infection compared to a no aerolysin control.

The enzyme was first tested on the parent Jurkat cells to confirm the removal of GPI-linked proteins and to establish conditions for the virus neutralization assay. Flow cytometry analysis showed that treatment of Jurkat cells with 20 mU/ml of PI-PLC removed approximately 90% of Thy-1 and CD59, based on mean total fluorescence counts (data not shown). When HIV-1 virus was treated with 50 mU/ml of PI-PLC, there was a substantial decrease in susceptibility to aerolysin neutralization FIG. 3), particularly at the lowest concentration of aerolysin (FIG. 3) where neutralization was reversed by 80to 90%. Complete reversal of neutralization was not expected as PI-PLC removal of GPI-anchored proteins is not quantitative. The pronounced decrease in aerolysin neutralization of HIV-1 we observed following enzyme treatment is further evidence that aerolysin acts directly on the virus and that, as with cells, GPI-linked proteins sensitize the virus to the toxin.

EXAMPLE 5
Proaerolysin Does Not Neutralize HIV-1

Figure 4:
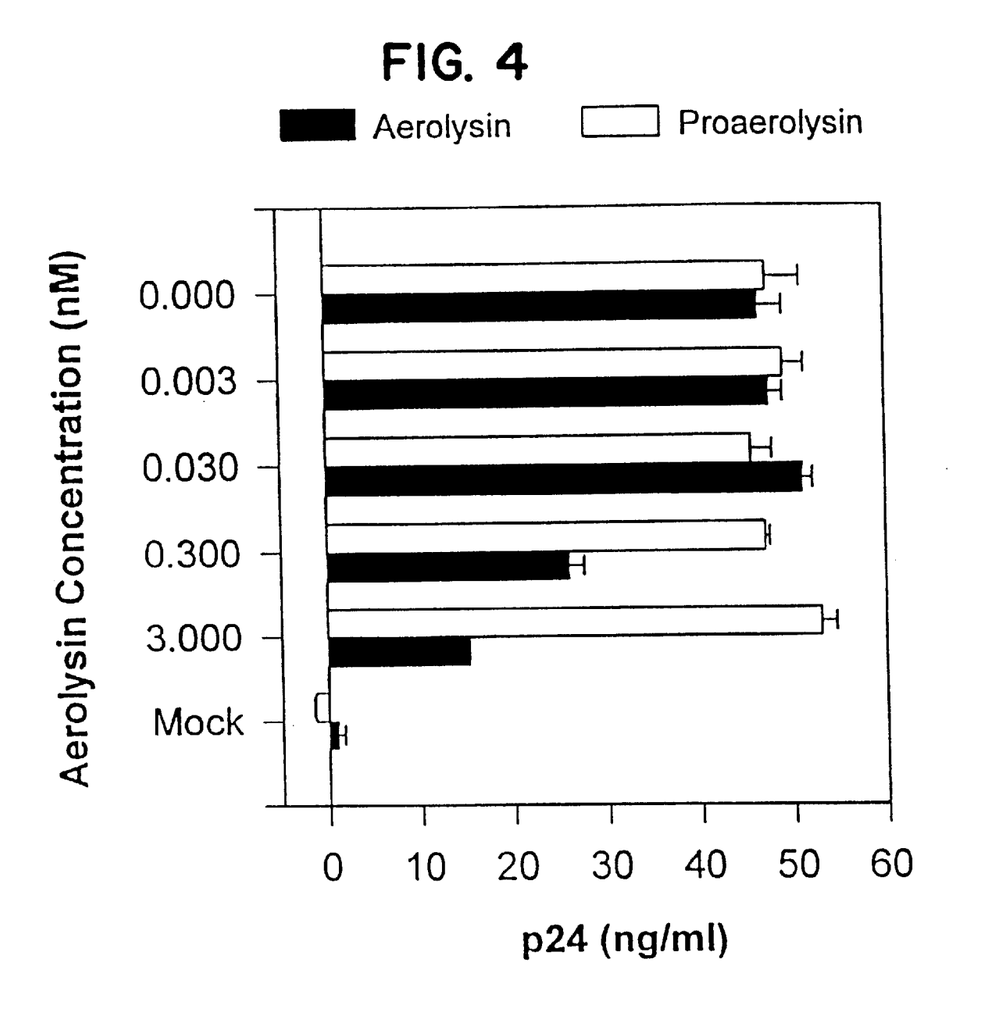

Aerolysin and proaerolysin can bind to GPI-anchored receptors equally well, but only aerolysin is capable of forming channels (Howard and Buckley, 1985). HIV-1 binding assays on aerolysin and proaerolysin confirmed that proaerolysin bound to the HIV-1 particles at least as well if not better than aerolysin (data not shown, also see FIG. 1). If aerolysin neutralization of HIV-1 was due simply to steric effects as a result of opsonization of the virus particles, then proaerolysin, which is slightly larger, should also neutralize the virus. The results in FIG. 4 show that this is not the case. Proaerolysin did not neutralize HIV-1 from Jurkat cells even at a concentration of 3 nM. In contrast, as seen in the previous experiments, aerolysin showed a dose dependent neutralization of the same virus. Similar observations were made in assays in which syncytium formation was used to score infection (data not shown).

EXAMPLE 6
Aerolysin Variants That Cannot Form Channels Do Not Neutralize HIV-1

The fact that the protoxin had no effect on HIV-1 led to the conclusion that binding to the receptors on the virus is not sufficient for neutralization. We also tested two inactive variants of the toxin. One of these, T253C/A300C is completely unable to form oligomers (Rossjohn et al., 1998)), whereas the other, Y221G, is unable to form a functional channel once it has oligomerized (unpublished observations; FIG. 2B). The results in FIG. 1A show that both of these variants are able to bind HIV-1 as well as the wild type protein, consistent with our observations that their binding to GPI-anchored proteins is unaffected. Oligomers of Y221G were detected on virus produced by Jurkat cells (FIG. 2B), confirming the ability of this variant to oligomerize. As expected, oligomers of T253C/A300C were not observed (FIG. 2B).

Neutralization assays revealed that neither of these two aerolysin variants was able to neutralize the virus from GPI-anchor positive Jurkat cells (data not shown). These data indicate that binding and oligomerization of the toxin on the surface of HIV-1 particles are not enough for neutralization. Insertion of the oligomer into the virus membrane to form the channel is also necessary.

EXAMPLE 7
Aerolysin Does Not Inhibit Viral Attachment to Soluble CD4Ig

Results of the above studies with proaerolysin and the aerolysin variants indicated that neutralization was not due to steric effects as a result of toxin binding or oligomerization. To confirm this, we studied the effect of aerolysin on HIV-1 binding to CD4, which is a necessary step in infection (REF). Formalin-fixed Staphylococcus.aureus cells, Cowan strain (SAC, Pansorbin) (Calbiochem, San Diego, Calif.) were washed twice with PBS and resuspended to 10% in PBS, 0.5% bovine serum albumin (BSA), 0.02% $NaN_3$. HIV-$1_{RF}$ supernatants (20 ng/ml of p24) were added to an equal volume of aerolysin dilutions (150 µl of $1 \times 10^{-8}$ to $1 \times 10^{-11}$ M) and incubated for 1 h at 37° C. Aliquots of 100 µl of the mixtures were then added to 100 µl of CD4Ig or human IgG1 at 50 µg/ml and incubated on ice for 1 h. Tubes were constantly mixed during the incubation. One hundred µl of washed SAC were then added to each tube and incubated for 1 h on ice. The complexes were washed 4 times with PBS. After the final wash, the complexes were resuspended in 300 µl of lysis buffer (1% Triton X-100, 50 mM Tris, pH 8, 5 mM EDTA, 100 mM NaCl) and incubated 30 min at room temperature. The SAC were pelleted by centrifugation and the lysates were then assayed for p24 in a standard ELISA.

Figure 5:
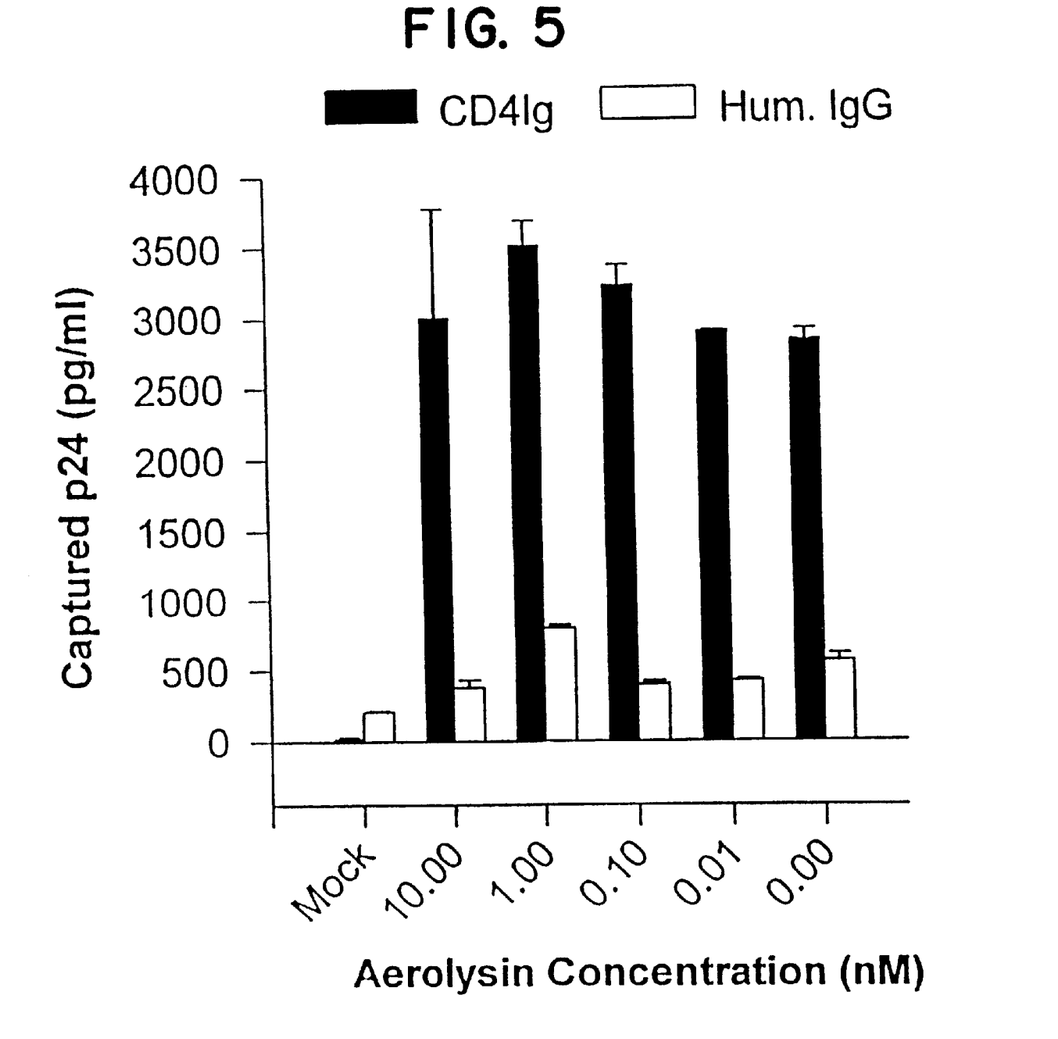

We treated GPI-anchor positive HIV-1 from Jurkat cells with dilutions of aerolysin before adding soluble CD4Ig or control human IgG1. The complexes were then precipitated with protein A-bearing SAC through the Fc regions of CD4Ig and IgG. The bound virus was lysed with detergent and released p24 was assayed. The results shown in FIG. 5 indicate that aerolysin does not block binding of virus to CD4 even at toxin concentrations as high as 10 nM.

EXAMPLE 8
Host Cells Are Not Killed by Aerolysin Delivered Via Fusion with HIV-1

Figure 6A:
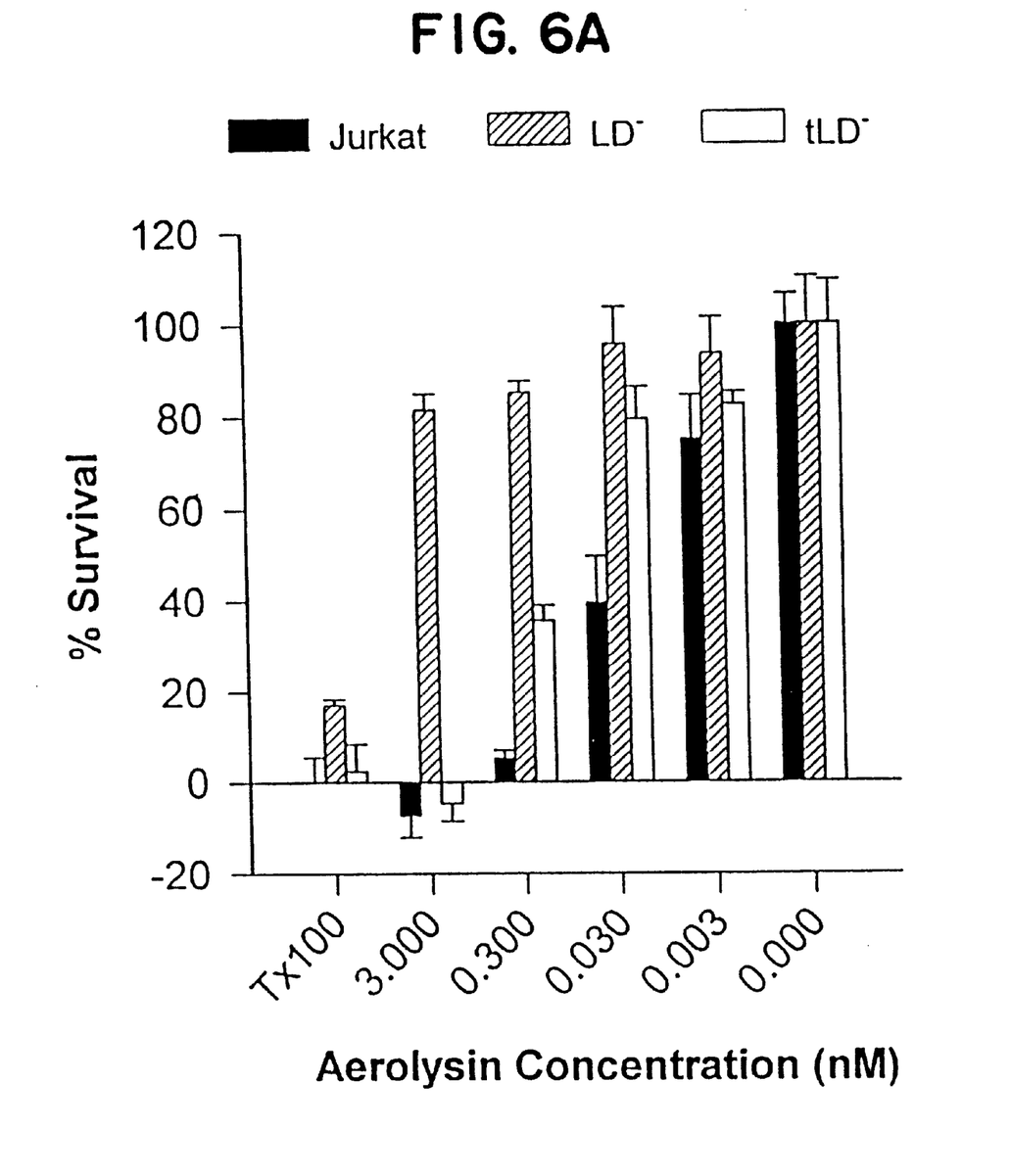
FIGS. 6A and 6B show that $LD^x$ cells are not killed by aerolysin-treated HIV-1. Cell viability assays in the presence of aerolysin were carried out as described in Example 3.
Figure 6B:
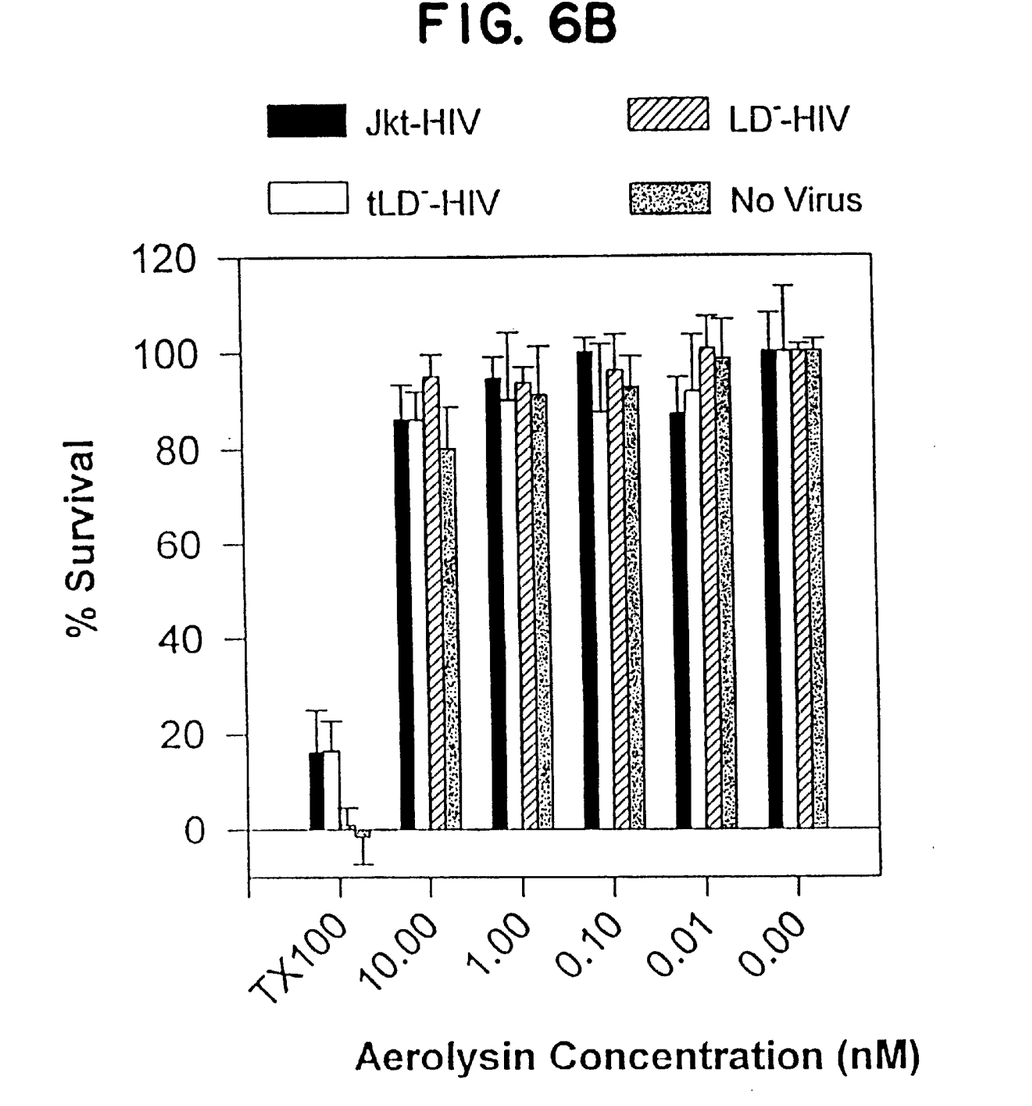

HIV particles that have aerolysin channels inserted in their envelopes could conceivably introduce the channels into cell membranes by fusion, thereby killing the cells. If this were the case, the neutralization we observed with increasing amounts of aerolysin could have been due to a failure to produce the virus because the cells were killed by the channels transferred by virus-cell fusion in the first stage of infection. To determine whether HIV-1 could deliver toxic levels of aerolysin to cells in this way, we studied the survival of LD$^-$ cells treated with HIV-1 that had been preincubated with aerolysin. We chose this cell line because the cells, lacking GPI-anchored proteins, are resistant to aerolysin and would not be killed by low concentrations of free toxin in our virus preparations. In a preliminary experiment we found that more than 90% of LD cells survived treatment with 3 nM aerolysin for 1 hour, whereas more than 95% of Jurkat cells were killed by 0.3 nM aerolysin (FIG. 6A). This result is consistent with earlier studies of the sensitivity of GPI-anchor-positive and negative cells to aerolysin toxicity (Nelson et al., 1997). We incubated virus produced by Jurkat, LD$^-$ cells or tLD$^-$ cells with aerolysin for 1 hour. The aerolysin-treated viruses were then added to LD$^-$ cells and after 2 hours cell viability was measured with MTS. No change in cell viability was seen with any of the viruses after a total exposure time of 4 hours, even when the virus had been pre-exposed to aerolysin concentrations as high as 10 nM and with virus concentrations of 20 ng/ml (p24) (FIG. 6B). This is clear evidence that HIV-1 does not kill cells by delivering the toxin to their plasma membranes during fusion.

REFERENCES

Abrami, L., Fivaz, M, Decroly, E., Seidah, N. G, Jean, F., Thomas, G., Leppla, S., Buckley, J. T. and van der Goot, F. G. (1998) The pore-forming toxin proaerolysin is activated by furin. *J. Biol. Chem.* (in press).

Aloia, R. C., Tian, H., and Jensen, F. C. (1993) *Proc. Natl. Acad. Sci. USA* 90: 5181–5185.

Ballard, J, Crabtree, J., Roe, B. A, and Tweten, R. K. (1995) The primary structure of *Clostricium septicum* alpha-toxin exhibits similarity with that of *Aeromonas hydrophila* aerolysin *Infect Immun.* 63:340–344.

Brodsky, R. A, Mukhina, G., Nelson, K. L., Lawrence, T. S., Jones, R. J., and Buckley, J. T. (1998) Resistance of paroxysmal nocturnal hemoglobinuria cells to the glycosylphosphatidylinositol-binding toxin aerolysin. *Blood* (in press)

Buckley, J. T. (1990) Purification of cloned proaerolysin released by a low protease mutant of *Aeromonas salmonicida*. *Biochem. Cell Biol* 68: 221–224.

Cowell, S., Aschauer, W., Gruber, H. J., Nelson, K. L., and Buckley, J. T. (1997) The erythrocyte receptor for the channel-forming toxin aerolysin is a novel glycosylphosphatidylinositol anchored protein. *Molec. Microb.* 25: 343–350.

Diep, D. B., Nelson, K. L., Raja, S. M., Pleshak, E. N., and Buckley, J. T. (1998) Glycosylphosphatidylinositol anchors of membrane glycoproteins are binding for the channel-forming toxin aerolysin. *J. Biol. Chem.* 273: 2355–2360.

Fontes, W., Sousa, M. V., Aragao, J. B., and Morhy, L. (1997) Determination of the amino acid sequence of the plant cytolysin enterolobin. *Arch. Biochem. Biophys.* 347:201–207.

Gomez, M. B., and Hildreth, J. E. K. (1995) *J. Virol* 69, 4628–4632 Hildreth, J. E. K., and Orentas, R. J. (1989) *Science* 244, 1075–1078 Howard, S. P., and Buckley, J. T. (1982) Membrane glycoprotein receptor and hole-forming properties of a cytolytic protein toxin. *Biochemistry* 21, 1662–1667.

Howard, S. P., and Buckley, J. T. (1985) Activation of the hole-forming toxin aerolysin by extracellular processing. *J. Bacteriol.* 163, 336–340.

Nelson, K. L., Raja, S. M., and Buckley, J. T. (1997) The glycosylphosphatidylinositol-anchored surface glycoprotein Thy-1 is a receptor for the channel-forming toxin aerolysin. *J. Biol. Chem.* 272: 12170–12174.

Nguyen, D. H., and Hildreth, J. E. K. (1998) *J. Virol,* submitted Orentas, R. J., and Hildreth, J. E. K. (1993) *AIDS Res. and Hum. Retrovir.* 9: 1157–1165

Parker, M. W., van der Goot, F. G., and Buckley, J. T. (1996) Aerolysin-the ins and outs of a channel-forming protein. *Molec. Microbiol* 19: 205–212.

Pinter, A., Honnen, W. J., Tilley, S. A., Bona, C., Zaghouani H., Gorny, M. K., and Zolla-Pazner, S. (1989) *J Virol* 63: 2674–2679.

Neville, D. M. (1971) Molecular weight determination of protein dodecyl sulphate complexes by gel electrophoresis in a discontinuous buffer system. *J Biol Chem* 246: 6328–6334.

Rodgers, W., and Rose, J. K. (1996) *J. Cell Biol.* 135: 1515–1523.

Rossjohn, J., Raja, S. M., Nelson, K. L., Feil, S. C., van der Goot, F. G., Parker, M. W., and Buckley, J. T. (1998) Movement of a loop in domain 3 of aerolysin is required for channel formation. *Biochemistry* 34: 741–746.

Sargiacomo, M., Sudol, M., Tang, Z., and Lisanti, M. P. (1993) *J. Cell Biol.* 122 789–807.

Sousa, M. V., Richardson, M., Fontes, W., and Morhy, L. (1994) Homology between the seed cytolysin enterolobin and bacterial aerolysins. *J. Prot. Chem.* 13:659–667.

Sousa, M. V. and Morhy, L. Enterolobin, a hemolytic protein from *Enterolobium contortisiliquum* seeds (*Leguminosae-Mimosoideae*). Purification and characterization. *An. Acad Bras. Cienc.* 61: 405–412.

Wyatt, R., and Sodorski, J. (1998) *Science* 280: 1884–1888.

We claim:

1. A method of treating a population of enveloped viruses which comprise a glycosylphosphatidylinositol-anchored protein in their membrane, the method comprising the step of:

contacting the population of enveloped viruses with an amount of a channel forming toxin which binds to glycosylphosphatidylinositol-anchors, wherein the amount is sufficient to reduce infectivity of the population of viruses by at least 50%.

2. The method of claim 1 wherein the viruses are retroviruses.

3. The method of claim 1 wherein the viruses are HIV-1.

4. The method of claim 1 wherein the toxin is aerolysin.

5. The method of claim 1 wherein the toxin is alpha toxin of *Clostridium septicum*.

6. The method of claim 1 wherein the toxin is enterolobin.

7. The method of claim 1 wherein the amount of toxin is sufficient to reduce infectivity of the population by at least 75%.

8. The method of claim 1 wherein the amount of toxin is sufficient to reduce infectivity of the population by at least 80%.

9. The method of claim 1 wherein the amount of toxin is sufficient to reduce infectivity of the population by at least 85%.

10. The method of claim 1 wherein the amount of toxin is sufficient to reduce infectivity of the population by at least 90%.

11. The method of claim 1 wherein the amount of toxin is sufficient to reduce infectivity of the population by at least 95%.

* * * * *